US009050435B2

(12) United States Patent
Lareau et al.

(10) Patent No.: US 9,050,435 B2
(45) Date of Patent: *Jun. 9, 2015

(54) HIGH FLOW CATHETERS

(75) Inventors: Raymond Lareau, Westford, MA (US); Benjamin Bell, Shrewsbury, MA (US); Mark Girard, Medway, MA (US)

(73) Assignee: AngioDynamics, Inc., Latham, NY (US)

( * ) Notice: Subject to any disclaimer, the term of this patent is extended or adjusted under 35 U.S.C. 154(b) by 112 days.

This patent is subject to a terminal disclaimer.

(21) Appl. No.: 13/053,428

(22) Filed: Mar. 22, 2011

(65) Prior Publication Data

US 2012/0245563 A1 Sep. 27, 2012

(51) Int. Cl.
*A61M 25/00* (2006.01)

(52) U.S. Cl.
CPC ....... *A61M 25/0026* (2013.01); *A61M 25/0043* (2013.01); *A61M 25/0054* (2013.01); *A61M 25/0028* (2013.01); *A61M 25/0068* (2013.01); *A61M 25/0023* (2013.01); *A61M 25/0029* (2013.01); *A61M 2025/0024* (2013.01); *A61M 2025/0037* (2013.01)

(58) Field of Classification Search
CPC ................ A61M 2025/0037; A61M 25/0068; A61M 25/0028; A61M 25/0023; A61M 25/0054; A61M 25/0043; A61M 25/0026; A61M 25/0029; A61M 2025/0024
USPC .......... 604/523, 533, 525, 96.01, 164.01, 264
See application file for complete search history.

(56) References Cited

U.S. PATENT DOCUMENTS

| 3,042,044 | A | * | 7/1962 | Sheridan | 604/104 |
|---|---|---|---|---|---|
| 3,094,124 | A | | 6/1963 | Birtwell | |
| 3,400,714 | A | * | 9/1968 | Sheridan | 128/207.18 |
| 3,438,375 | A | | 4/1969 | Ericson | |
| 3,978,157 | A | | 8/1976 | Bottenbruch et al. | |
| 4,054,139 | A | | 10/1977 | Crossley | |
| 4,142,525 | A | | 3/1979 | Binard et al. | |
| 4,403,983 | A | | 9/1983 | Edelman et al. | |

(Continued)

FOREIGN PATENT DOCUMENTS

| DE | 20208420 | 10/2002 |
|---|---|---|
| EP | 0328421 | 8/1989 |

(Continued)

OTHER PUBLICATIONS

Carbothane MSDS from Microspecorporation.com accessed Thursday Aug. 4, 2011. http://www.microspecorporation.com/materials.php?id=5 (1 page).
Carbothane MSDS from msds.carboline.com accessed Thursday Aug. 4, 2011. http://msds.carboline.com/website/carbmsds.nsf%28all%29/87496753746CA5888525705A004343CE8/$file/Carbothane+134+HG+PDS+3-11.pdf (2 pgs.).

(Continued)

*Primary Examiner* — Theodore Stigell
*Assistant Examiner* — Lauren M Peng
(74) *Attorney, Agent, or Firm* — Peter J. Flora

(57) ABSTRACT

A catheter that comprises a hub, an elongated conduit, and at least one lumen therein. The lumen includes a proximal lumen section, a distal lumen section, and an intermediate lumen section extending between the proximal and distal lumen sections. The cross-sectional dimension of the intermediate lumen section is less than the cross-sectional dimension of the distal lumen section. In one embodiment, the cross-sectional dimension of the intermediate lumen section is less than the cross-sectional dimension of the proximal lumen section. In certain embodiments, the lumen tapers from the distal and/or proximal lumen sections to the intermediate lumen section.

7 Claims, 6 Drawing Sheets

(56) References Cited

U.S. PATENT DOCUMENTS

| | | | |
|---|---|---|---|
| 4,423,740 A | 1/1984 | Castle et al. | |
| 4,468,224 A | 8/1984 | Enzmann et al. | |
| 4,469,483 A | 9/1984 | Becker et al. | |
| 4,483,688 A | 11/1984 | Akiyama | |
| 4,563,180 A | 1/1986 | Jervis et al. | |
| 4,569,673 A | 2/1986 | Tesi | |
| 4,592,920 A | 6/1986 | Murtfeldt | |
| 4,603,152 A | 7/1986 | Laurin et al. | |
| 4,623,327 A | 11/1986 | Mahurkar | |
| 4,769,005 A | 9/1988 | Ginsburg et al. | |
| 4,902,503 A | 2/1990 | Umemura et al. | |
| 4,944,726 A | 7/1990 | Hilal et al. | |
| 5,019,096 A | 5/1991 | Fox et al. | |
| 5,059,170 A | 10/1991 | Cameron | |
| 5,125,893 A | 6/1992 | Dryden | |
| 5,133,742 A | 7/1992 | Pinchuk | |
| 5,151,231 A | 9/1992 | Lambert et al. | |
| 5,205,834 A | 4/1993 | Moorehead et al. | |
| 5,229,431 A | 7/1993 | Pinchuk | |
| 5,249,598 A | 10/1993 | Schmidt | |
| 5,300,048 A | 4/1994 | Drewes et al. | |
| 5,374,245 A | 12/1994 | Mahurkar | |
| 5,403,291 A | 4/1995 | Abrahamson | |
| 5,405,340 A | 4/1995 | Fageol et al. | |
| 5,472,417 A | 12/1995 | Martin et al. | |
| 5,509,897 A | 4/1996 | Twardowski et al. | |
| 5,542,937 A | 8/1996 | Chee et al. | |
| 5,569,182 A | 10/1996 | Twardowski et al. | |
| 5,575,769 A | 11/1996 | Vaillancourt | |
| 5,614,136 A | 3/1997 | Pepin et al. | |
| 5,662,913 A | 9/1997 | Capelli | |
| 5,683,640 A | 11/1997 | Miller et al. | |
| 5,725,510 A | 3/1998 | Hartmann et al. | |
| 5,800,414 A | 9/1998 | Cazal | |
| 5,843,161 A | 12/1998 | Solovay | |
| 5,879,499 A | 3/1999 | Corvi | |
| 5,928,174 A | 7/1999 | Gibbins | |
| 6,033,393 A | 3/2000 | Balbirz et al. | |
| 6,093,180 A | 7/2000 | Elsberry | |
| 6,177,522 B1 | 1/2001 | Brady et al. | |
| 6,197,846 B1 | 3/2001 | Combe et al. | |
| 6,200,338 B1 | 3/2001 | Solomon et al. | |
| 6,217,566 B1 | 4/2001 | Ju et al. | |
| 6,227,200 B1 | 5/2001 | Crump et al. | |
| 6,280,423 B1 | 8/2001 | Davey et al. | |
| 6,315,789 B1 | 11/2001 | Cragg | |
| 6,355,858 B1 | 3/2002 | Gibbins | |
| 6,368,658 B1 | 4/2002 | Schwarz et al. | |
| 6,375,637 B1 | 4/2002 | Campbell et al. | |
| 6,409,700 B1 | 6/2002 | Siegel, Jr. et al. | |
| 6,442,415 B1 | 8/2002 | Bis et al. | |
| 6,446,671 B2 | 9/2002 | Armenia et al. | |
| 6,517,520 B2 | 2/2003 | Chang et al. | |
| 6,530,951 B1 | 3/2003 | Bates et al. | |
| 6,545,097 B2 | 4/2003 | Pinchuk et al. | |
| 6,595,966 B2 | 7/2003 | Davey et al. | |
| 6,605,751 B1 | 8/2003 | Gibbins et al. | |
| 6,663,614 B1 * | 12/2003 | Carter | 604/525 |
| 6,777,466 B2 | 8/2004 | Eckstein et al. | |
| 6,819,951 B2 | 11/2004 | Patel et al. | |
| 6,897,349 B2 | 5/2005 | Gibbins et al. | |
| 6,938,668 B2 | 9/2005 | Whicher et al. | |
| 7,179,849 B2 | 2/2007 | Terry | |
| 7,264,858 B2 | 9/2007 | Belliveau et al. | |
| 7,410,602 B2 | 8/2008 | Davey et al. | |
| 7,846,134 B1 * | 12/2010 | Nadolski et al. | 604/164.11 |
| 2001/0037065 A1 | 11/2001 | Graf et al. | |
| 2002/0082559 A1 | 6/2002 | Chang et al. | |
| 2002/0091362 A1 | 7/2002 | Maginot et al. | |
| 2002/0156430 A1 | 10/2002 | Haarala et al. | |
| 2003/0065355 A1 | 4/2003 | Weber | |
| 2003/0153983 A1 | 8/2003 | Miller et al. | |
| 2003/0203991 A1 | 10/2003 | Schottman et al. | |
| 2004/0068241 A1 | 4/2004 | Fischer, Jr. | |
| 2004/0068251 A1 | 4/2004 | Chan et al. | |
| 2004/0068315 A1 | 4/2004 | Chandrasekaran et al. | |
| 2004/0073171 A1 | 4/2004 | Rogers et al. | |
| 2004/0076582 A1 | 4/2004 | DiMatteo et al. | |
| 2004/0131863 A1 | 7/2004 | Belliveau et al. | |
| 2004/0171747 A1 | 9/2004 | Zhong | |
| 2004/0199128 A1 | 10/2004 | Morris et al. | |
| 2004/0199192 A1 * | 10/2004 | Akahoshi | 606/169 |
| 2004/0220534 A1 | 11/2004 | Martens et al. | |
| 2004/0266301 A1 | 12/2004 | Vedula et al. | |
| 2005/0010275 A1 | 1/2005 | Sahatjian et al. | |
| 2005/0013988 A1 | 1/2005 | Fu et al. | |
| 2005/0119724 A1 | 6/2005 | Phaneuf et al. | |
| 2005/0131356 A1 | 6/2005 | Ash et al. | |
| 2005/0182352 A1 | 8/2005 | DiMatteo et al. | |
| 2005/0192546 A1 | 9/2005 | Grieg et al. | |
| 2005/0216074 A1 | 9/2005 | Sahatjian et al. | |
| 2005/0234388 A1 | 10/2005 | Amos et al. | |
| 2006/0004325 A1 | 1/2006 | Hamatake et al. | |
| 2006/0052757 A1 | 3/2006 | Fischer et al. | |
| 2006/0189922 A1 | 8/2006 | Amarasinghe et al. | |
| 2006/0264912 A1 | 11/2006 | McIntyre et al. | |
| 2007/0043390 A1 * | 2/2007 | Neilan | 606/200 |
| 2007/0225661 A1 * | 9/2007 | Ash et al. | 604/284 |
| 2007/0299043 A1 | 12/2007 | Hunter et al. | |
| 2008/0051759 A1 | 2/2008 | Murphy et al. | |
| 2008/0086096 A1 | 4/2008 | Vonyakovski et al. | |
| 2008/0108975 A1 | 5/2008 | Appling et al. | |
| 2008/0234659 A1 | 9/2008 | Cheng et al. | |
| 2009/0036768 A1 | 2/2009 | Seehusen et al. | |
| 2009/0171319 A1 | 7/2009 | Guo et al. | |
| 2009/0171436 A1 | 7/2009 | Casanova et al. | |
| 2009/0326560 A1 | 12/2009 | Lampropoulos et al. | |

FOREIGN PATENT DOCUMENTS

| | | |
|---|---|---|
| EP | 0589577 | 3/1994 |
| EP | 0987042 | 3/2000 |
| FR | 2718969 | 10/1995 |
| JP | 2001172848 | 6/2001 |
| JP | 2001340466 | 12/2001 |
| JP | 2003037632 | 2/2003 |
| JP | 2006296694 | 11/2006 |
| WO | WO-96/41649 | 12/1996 |
| WO | WO-97/10858 | 3/1997 |
| WO | WO-99/38550 | 8/1999 |
| WO | WO-99/42156 | 8/1999 |
| WO | WO-00/53253 | 9/2000 |
| WO | WO-01/70324 | 9/2001 |
| WO | WO-2006/058042 | 6/2006 |

OTHER PUBLICATIONS

"AgION's Silver Copper Zeolite Okayed by FDA for Food Contact," AgION Technologies, Inc., http://www.agion-tech.com/NewsDetail.asp?PressID=91, 2 pages (2005).

"Anatomy and Placement," http://www.rnceus.com/picc/piccanat.html, 2 pages (2005).

"Application Guide," Spire Corporation, http://www.spirebiomedical.com/Biomedical/app_guide.html, 3 pgs (2005).

"Biocompatibles—Advanced Biomedical Polymers," http://www.pharmaceutical-technology.com/contractors/drug_delivery/biocompatibles, 3 pages (2005).

"Broviac Catheters, PICC Lines and Other Catheters," The American Pediatric Surgical Association, http://www.eapsa.org/parents/catheter.htm, 13 pages (2005).

"Central Venous Catheters," http://academic.luzerne.edu/nfrusciante/nur204/powerpoints/cvc.pdf, 11 pages (2005).

"Description of Ion Beam Assisted Deposition Process," Spire Corporation, http://www.spirebiomedical.com/Biomedical/ionbeam.html, 2 pages (2005).

"Description of Ion Implantation Process," Spire Corporation, http://www.spirebiomedical.com/Biomedical/ionimpl.html, 4 pages (2005).

"Electrically Ionized Metals for the Prevention of Catheter Colonization with Microorganisms," The University of Texas MD Anderson Cancer Center, Office of Technology Development, http://www.mdanderson.org/departments/techcommerc, 2 pages(2005).

(56) References Cited

OTHER PUBLICATIONS

"FAQ: Electroplating—How It Works," http://www.finishing.com/faqs/howworks.html, 4 pages (2005).
"Fighting Infections, Healing Wounds," AcryMed, Inc., http://www.acrymed.com, 1 page (2005).
"Flexima™ Tight Loop All-Purpose Drainage Catheters," Boston Scientific Corporation, http://www.bostonscientific.com, 1 page (2005).
Gibbins, "SilvaGard™ Technology Summary," AcryMed, Inc., http://www.acrymed.com/pdf%20files/bpease_silvgrd.pdf, 8 pages (2006).
Gibbins et al., "The Role of Antimicrobial Silver Nanotechnology," Medical Device & Diagnostic Industry, http://www.devicelink.com/mddi/archive/05/08/005.html, 6 pages (2005).
"Ion Beam Processing (IBP) Technologies—Sector Study," BDM Federal Inc., prepared for the North American Technology and Industrial Base Organization (NATIBO), 133 pages (1996).
"Ion-Sight™," Spire Corporation, http://www.spirebiomedical.com/Biomedical/Ionsight.html, 2 pages (2005).
Management of a PICC Line (Peripherally Inserted Central Catheter), CancerBACUP, http://www.cancerbacup.org.uk/Treatments/Chemotherapy/Linesports/PICCline, 4 pages (2005).
"New Multifunctional Textiles: Antimicrobial Treatments," Intelligent Textile Structures—Application, Production & Testing, International Workshop, Thessaloniki, Greece, Amphitheater of Thessaloniki Technology Park, 31 pages (2005).
Oberst, "Researchers Describe How to Put the 'Nano' in Synthetic Polymers," Cornell Chronicle, http://www.news.cornell.edu/Chronicle/04/6.10.04/CCMR-POP_conf.html, 2 pages (2004).
"ON-Q C-Bloc Continuous Nerve Block System," I-Flow Corporation, http://www.iflo.com/prod_ong_classic.php, 7 pages (2005).
"ON-Q® PainBuster® Post-Op Pain Relief System," I-Flow Corporation, http://www.iflo.com/prod_ong_classic.php, 7 pages (2005).
Powers, "Antimicrobial Silver Nanoparticles Eliminate Biofilm Formation on Medical Devices," NanoBiotech News, vol. 3, No. 30, 2 pages (2005).
"Process Services," Spire Corporation, http://www.spirebiomedical.com/Biomedical/process_serv.html, 2 pages (2005).
Rosenthal, "PICC Line," University of Illinois Medical Center at Chicago, http://uimc.discoveryhospital.com/main.php?t=enc&id=3017, 2 pages (2005).
"SilvaGard™ Antimicrobial Surface Treatment," AcryMed, Inc., http://www.acrymed.com/techATD.htm, 2 pages (2005).
"Silver Catheter Destroys Bacterial Paradise," NewsDesk No. 9820, Siemens AG, http://w4.siemens.de/en2/html/press/newsdesk_archive/1998/e_9820_d.html, 2 pages (1998).
Sobie, "*Ion Beam Technology for Thin Film Applications*," edited from a reprint of Vacuum & Thinfilm, 6 pages (2001).
"SPI-Argent™," Spire Corporation, http://www.spirebiomedical.com/Biomedical/SPIargent.html, 2 pages (2005).
"Tal MicroDrainage™ Set," Boston Scientific Corporation, http://www.bostonscientific.com, 2 pages (2005).
"Technology Overview," Spire Corporation, http://www.spirebiomedical.com/Biomedical/techoverview.html, 1 page (2005).
"Types of CV ADs," Hemophilia Galaxy, http://www.hemophiliagalaxy.com/patients/managing/va_central/types.html, 3 pages (2005).
"Vaxcel® Implantable Ports with PASV® Valve Technology," Boston Scientific Corporation, http://www.bostonscientific.com, 3 pages (2005).
"Vaxcel® Implantable Ports with PASV® Valve Technology—Port Design Options," Image, Boston Scientific Corporation, http://www.bostonscientific.com (2005).
"Vaxcel® Peripherally Inserted Central Catheter (PICC)," Boston Scientific Corporation, http:www.bostonscientific.com, 3 pages (2005).
"Vaxcel® Peripherally Inserted Central Catheter (PICC)—Instructions for Use," Boston Scientific Corporation, http://www.bostonscientific.com, 3 pages (2005).
"Vaxcel® Peripherally Inserted Central Catheter (PICC)—Product Information" Boston Scientific Corporation, http://www.bostonscientific.com, 3 pages (retrieved from the internet prior to the filing of the application), Nov. 15, 2005.
"Vaxcel® Plus Chronic Dialysis Catheter," Boston Scientific Corporation, http://www.bostonscientific.com, 2 pages (2005).
"Vaxcel® Tunneled Central Venous Catheter," Boston Scientific Corporation, http://www.bostonscientific.com, 5 pages (2005).
"Vaxcel® Tunneled Central Venous Catheters—Product Information," Boston Scientific Corporation, http://www.bostonscientific.com, 3 pages (retrieved from the internet prior to filing of the application).
"Venous Access Device Insertion and Maintenance," Boston Scientific Corporation, http://www.bostonscientific.com/templatedata/imports/HTML/infusion_therapy/index.html, 1 page (2005).
Zschaler, "Testing of the Antimicrobial Effect of Catheter Tubing with a Roll Culture Method," 4 pages (2005).
Hunter et al., "Anti-Scarring Drug Combinations and Use Thereof," U.S. Appl. No. 60/723,053 Specification (2005).
J.A. Zawacki, "Carbothane Fixed Split-Tip Dialysis Catheters for Longer-Term Haemodialysis," Business Briefing: Global Healthcare—Advanced Medical Technologies, pp. 1-2 (2004).
Thermedics Polymer Products, "Committed to Providing Medical Grade Thermoplastic Polyurethane Resins," http://www.viasys.tv/prod_serv/downloads/139_Brochure.pdf, pp. 1-8 (2005).
"HemoSplit Catheter, 510(k), Summary of Safety and Effectiveness, 21 CFR 807.92(a)," (2003).
"Noveon, Medical Urethanes," http://www.estane.com/technology/Medical.asp, pp. 1-6 (2005).
"Vaxcel® Plus Chronic Dialysis Catheter," http://www.bostonscientific.com/med_specialty/deviceDetail.jsp?task=tskBasicDevice.jsp&sectionId=4&re1ID=4,178,179,180&deviceId=13015&uniqueId=MPDB3839, (2007).
T.M. Vesely, "Tunneled Catheter Design: Does it Matter? (Lecture)," The Journal of Vascular Access, vol. 6, pp. 132-136 (2005).
Asch, "Venous access: options, approaches and issues," Can Assoc. Radiol J., vol. 52, No. 3 pp. 153-164 (2001).
Herts et al., "Power injection of contrast media using central venous catheters: feasibility, safety, and efficacy," AJR Am. J. Roentgenol., vol. 176, No. 2, pp. 447-453 (2001).
Roth et al., "Influence of radiographic contrast media viscosity to flow through coronary angiographic catheters," Cathet. Cardiovasc. Diagn., vol. 22, No. 4, pp. 290-294 (1991).
Carlson et al., "Safety considerations in the power injection of contrast media via central venous catheters during computered tomogrphic examinations," Invest. Radiol., vol. 27, No. 5, p. 337-340 (1992).
Kaste et al., "Safe use of powr injectors with central and peripheral venous access devices for pediatric CT," Pediatr. Radiol., vol. 26, No. 8, pp. 449-501 (1996).
Herts et al., "Power injection of intravenous contrast material through central venous catheters for CT: in vitro evaluation," Radiology, vol. 200, No. 3, pp. 731-735 (1996).
Rivitz et al., "Power injection of peripherally inserted central catheters," J. Vasc. Interv. Radiol., vol. 8, No. 5, pp. 857-863 (1997).
Rogalla et al., Safe and easy power injection of contrast material through a central line, Eur. Radiol., vol. 8, No. 1, pp. 148-149 (1998).
Williamson et al., "Assessing the adequacy of peripherally inserted central catheters for power injection of intravenous contrast agents for CT," J. Comput. Assist. Tomogr., vol. 25, No. 6, pp. 932-937 (2001).
Chahoud et al., "Randomized comparison of coronary angiography using 4F catheters: 4F manual versus 'Acisted' power injection technique," Catheter Cardiovasc. Interv., vol. 53, No. 2, pp. 221-224 (2001).
Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).
Saito et al., "Diagnostic brachial coronary arteriography using a power-assisted injector and 4 French catheters with new shamps," J. Invasive Cardiol., vol. 9, No. 7, pp. 461-468 (1997).

\* cited by examiner

HIGH FLOW CATHETERS

FIELD OF THE INVENTION

This invention relates to indwelling catheters that result in increased fluid flow and catheter strength.

BACKGROUND

High flow rates through catheters are necessary to maximize the efficiency of medical procedures such as dialysis and the introduction of contrast in so-called "power injection" procedures. Certain catheter designs have been developed to increase flow rates, such as in U.S. Pat. Nos. 7,410,602, 6,595,966, and 6,280,423, each of which is incorporated herein by reference, but there remains a growing need for catheters that can accommodate increased flow rates. There is also a need for very small diameter catheters for positioning in smaller bodily lumens, yet allowing for high flow rates and requiring high mechanical strength.

SUMMARY OF THE INVENTION

In one aspect, the present invention includes a catheter that comprises a hub, an elongated conduit, and at least one lumen therein. The lumen includes a proximal lumen section, a distal lumen section, and an intermediate lumen section extending between the proximal and distal lumen sections. In one embodiment, a cross-sectional dimension of the intermediate lumen section is less than a cross-sectional dimension of the distal lumen section. In another embodiment, a cross-sectional dimension of the intermediate lumen section is less than a cross-sectional dimension of the proximal lumen section. In certain embodiments, the lumen tapers from the distal and/or proximal lumen sections to the intermediate lumen section.

In certain embodiments, the elongated conduit of the catheter includes a proximal conduit section, a distal conduit section, and an intermediate conduit section extending between the proximal and distal conduit sections. Each of the proximal, intermediate, and distal conduit sections is characterized by an outer cross-sectional dimension. In some embodiments, the outer cross-sectional dimension of the intermediate conduit section is less than the outer cross-sectional dimensions of either or both of the proximal and/or distal conduit sections.

In certain embodiments, the wall thickness of the elongated conduit is greater at the proximal and/or distal conduit sections than at the intermediate conduit section.

In another aspect, the present invention includes a method of making a catheter of the present invention. In certain embodiments, the method will comprise a process of extrusion in which the plastic drawdown is varied programmatically. In alternate embodiments, an internal pressure may be applied within the lumen of the catheter, which pressure optionally varies from the pressure external to the catheter, to create variation in the outer diameter of the catheter or in the wall thickness.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION OF PREFERRED EMBODIMENTS

The present invention relates to catheters designed for high flow rates and to methods for making and using such catheters. In certain embodiments, the present invention makes use of individual or opposing tapers along an indwelling catheter shaft to impart the catheter with increased durability and improved flow dynamics, both for the overall catheter system and localized at the catheter tip, when compared to conventional catheter devices. For certain applications such as venous access devices, the present invention enables the positioning of the smallest diameter portions of the catheter within small veins, such as in the arm, while allowing for the positioning of a larger catheter diameter portion within the great vessels of the chest, such as the superior vena cava. The designs and methods of the present invention apply equally to single lumen and double (or more) lumen embodiments.

Figure 1:
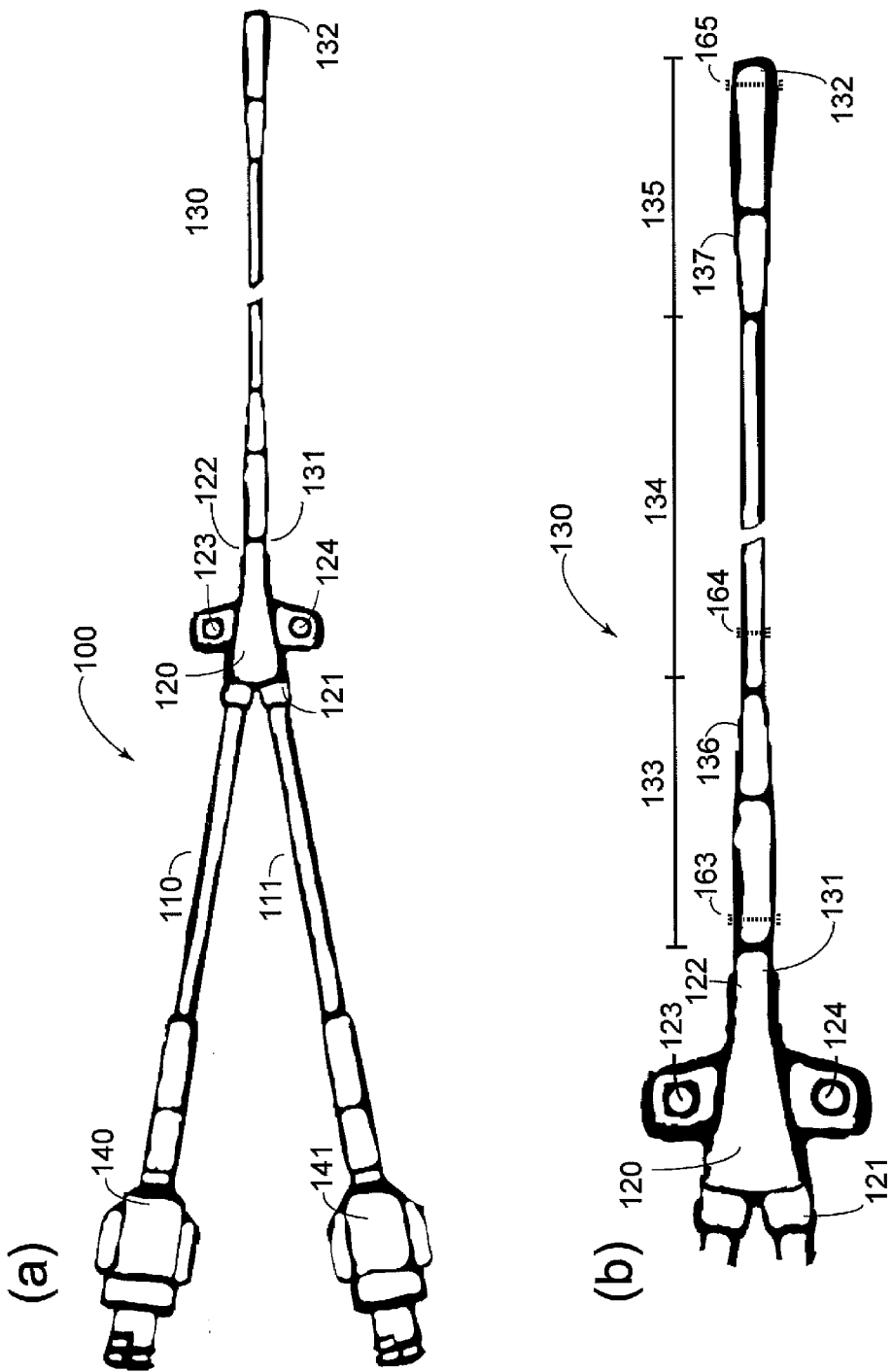
FIGS. 1(a) and 1(b) show catheter devices in accordance with an embodiment of the present invention.
Figure 2:
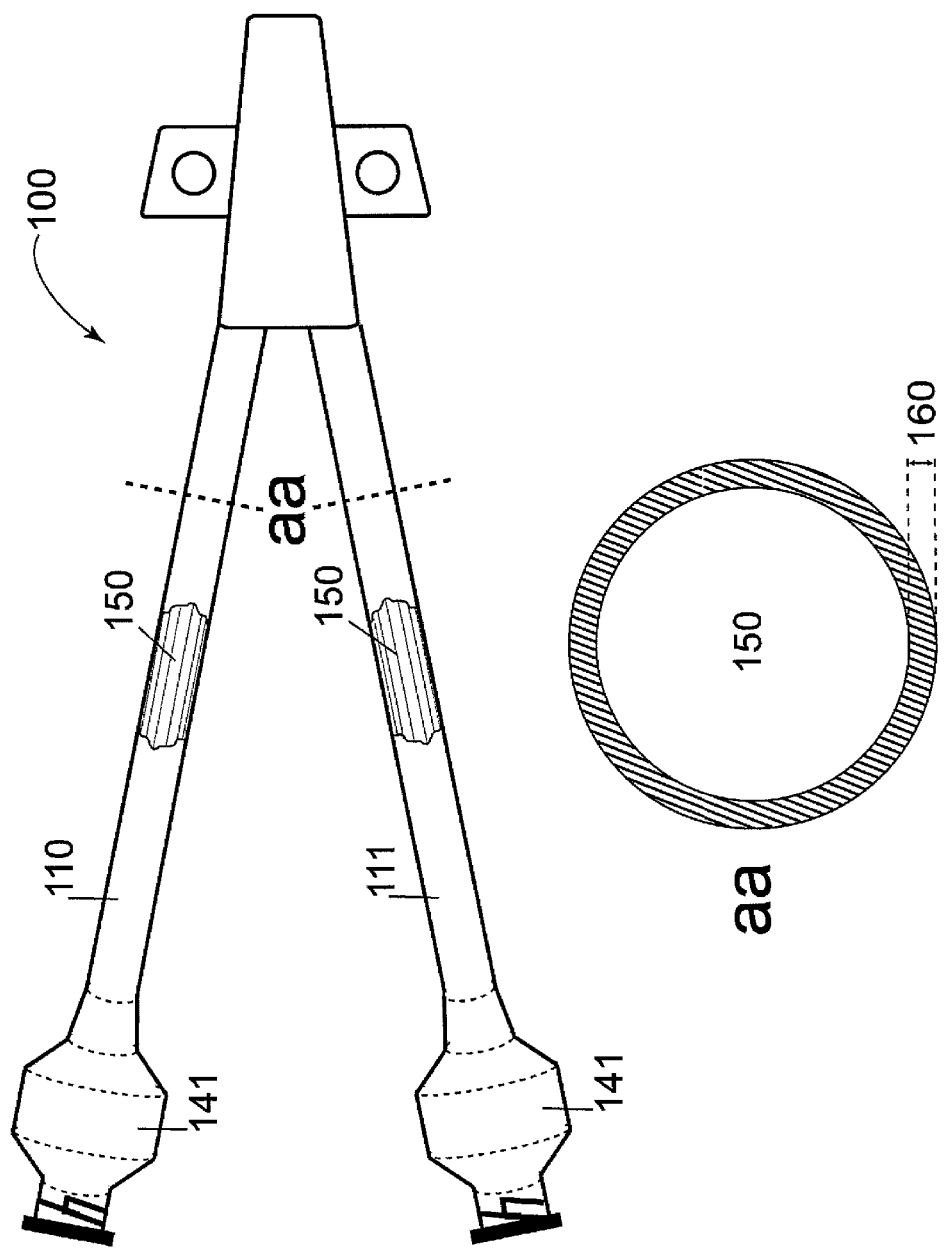
FIG. 2 is a side and cross sectional view of a catheter device in accordance with an embodiment of the present invention.
Figure 3:
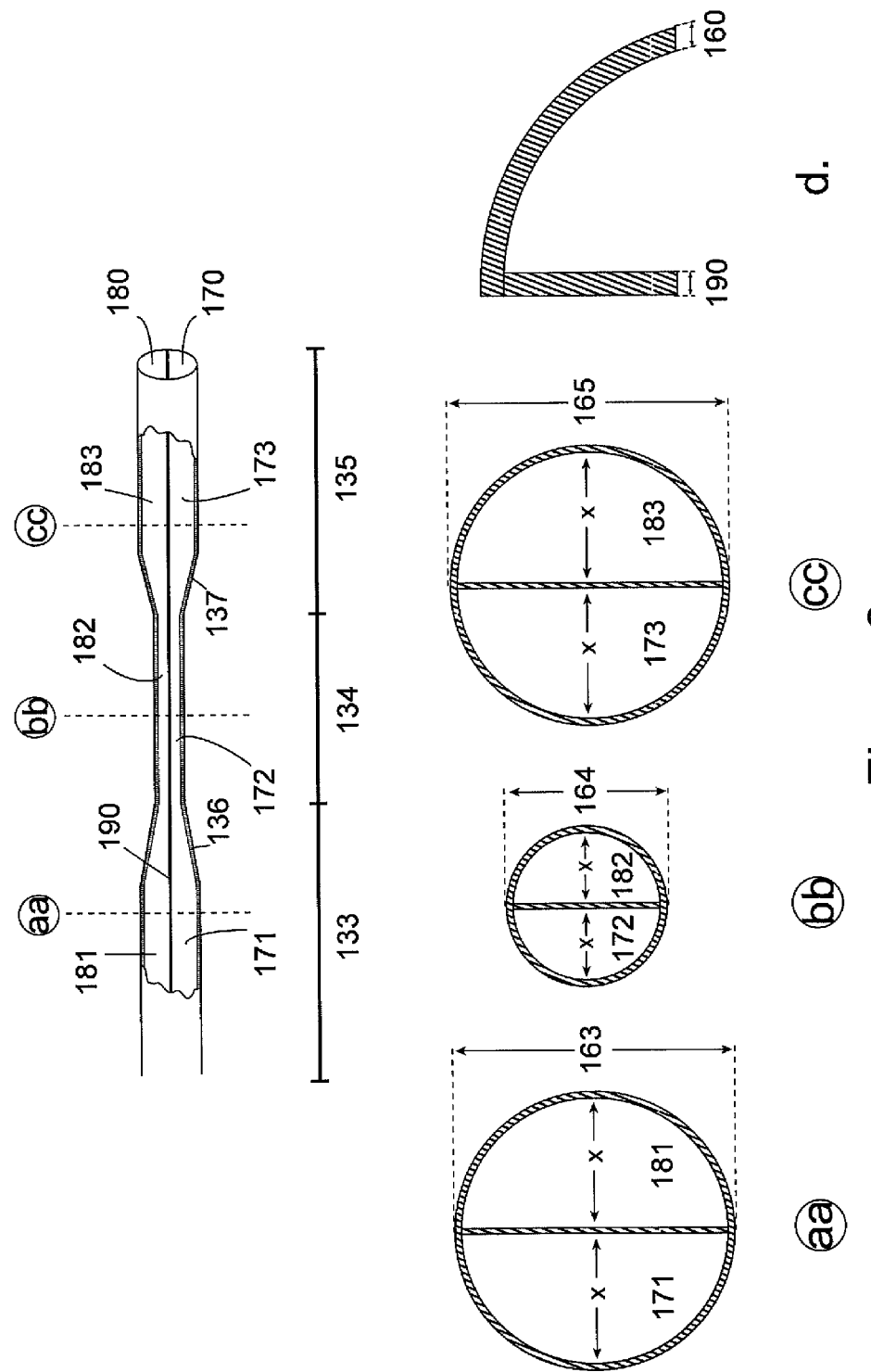
FIG. 3 includes side and cross-sectional views of a catheter device in accordance with an embodiment of the present invention.

FIGS. 1-3 illustrate one embodiment of the present invention. Catheter 100 is a dual lumen peripherally inserted central catheter (PICC) that includes first and second connecting portions 110, 111, each connected to a proximal portion 121 of hub 120, and an elongated conduit 130 connected to a distal portion 122 of hub 120. Each of the first and second connecting portions 110, 111 have an open lumen extending therein along their length. In one embodiment, one or both of the connecting portions 110, 111 include in-line valves 140, 141, such as a PASV™ valve (Navilyst Medical, Inc., Marlborough, Mass.) as described in U.S. Pat. No. 5,205,834, which is incorporated herein by reference. Alternatively, one or both of the connecting portions 110, 111 include line clamps (not shown) which may be actuated to restrict or prevent flow therethrough, as is known in the art. As shown in FIG. 2, each of the first and second connecting portions 110, 111 has a lumen 150 therein having substantially constant cross-sectional dimension (e.g., diameter), and an appropriate wall thickness 160 depending upon the operational requirements of the catheter 100.

The elongated conduit 130 includes a proximal end 131, a distal end 132, a proximal conduit section 133, an intermediate conduit section 134, and a distal conduit section 135. Each of the conduit sections 133, 134, and 135 is characterized by an outer cross-sectional dimension (e.g., diameter) 163, 164, and 165, respectively. In a preferred embodiment as shown in FIG. 3, the outer cross-sectional dimensions 163, 165 of the proximal and distal conduit sections 133, 135 are each greater than the outer cross-sectional dimension 164 of the intermediate conduit section 134. In other embodiments, either one (but not both) of the outer cross-sectional dimensions 163, 165 of the proximal and distal conduit sections 133, 135 is greater than the outer cross-sectional dimension 164 of the intermediate conduit section 134. The elongated conduit preferably includes at least one of a proximal taper segment 136 between the proximal conduit section 133 and the intermediate conduit section 134, and/or a distal taper segment 137 between the intermediate conduit section 134 and the distal conduit section 135. The outer cross-sectional dimension (e.g., diameter) of the taper segments 136, 137 gradually transitions from the connected conduit sections.

In the embodiment of FIGS. 1-3, the elongated conduit 130 includes two lumens 170, 180 extending between its proximal and distal ends 131, 132. Each of the lumens 170, 180 includes a proximal lumen section 171, 181, an intermediate lumen section 172, 182, and a distal lumen section 173, 183, respectively. The proximal, intermediate, and distal lumen sections generally correspond to the proximal, intermediate, and distal conduit sections, respectively. As shown in FIGS. 3a, 3b, and 3c, each of the lumens 170, 180 is characterized by a cross-sectional dimension "x" in each of the proximal (as shown in FIG. 3a), intermediate (as shown in FIG. 3b), and distal lumen sections (as shown in FIG. 3c). In this embodiment, the cross-sectional dimension of both lumens 170, 180 within the proximal and distal lumen sections (171, 181 and 173, 183) are each greater than the cross-sectional dimension of the lumens 170, 180 within the intermediate lumen sections (172, 182). In other embodiments, the cross-sectional dimensions of the lumens 170, 180 are greater within either one (but not both) of the proximal and distal lumen sections (171, 181 and 173, 183) when compared with the respective intermediate lumen sections (172, 182). Preferably, changes in the outer cross-sectional dimension of the conduit 130 reflect likewise changes in the cross-sectional dimensions of the lumens within the conduit 130. As such, in the optional taper segments 136, 137, the cross-sectional dimension of the lumens 170, 180 gradually transition between the corresponding proximal, intermediate, and distal lumen sections. In other embodiments, an increase in the outer cross-sectional dimension of the conduit 130 does not reflect a corresponding increase in the cross-sectional dimension of the lumen(s) within the conduit 130, thus resulting in an increased wall thickness and a corresponding increase in catheter strength and rigidity.

The embodiment shown in FIGS. 1-3 is characterized by an increased durability over conventional catheters, owing to the relatively large cross-sectional dimensions, and corresponding enhanced mechanical properties, at the proximal and distal ends of the elongated conduit where stresses on the device are high from normal use. Moreover, enhanced fluid flow is achieved at the distal end of the catheter, where relatively large cross-sectional lumen dimensions allow for diffusion of the flow over a larger area at the catheter exit to reduce the velocity and force of the exiting fluid during injection, such as during power injection or infusion with a syringe. Additionally, it is believed that a larger lumen dimension at the catheter distal tip helps prevent lumen occlusion and thrombosis.

The lumens 170, 180 are of any suitable shape, as is known in the art. For example, when the catheters of the present invention include two lumens, their shape is preferably D-shaped, as shown in FIGS. 3a, 3b, and 3c. Alternatively, the lumens may be circular, ovular, triangular, rectangular, or other suitable shape. When the catheters of the present invention include only a single lumen, its shape is preferably circular such that its cross-sectional dimension is a diameter.

When in use, the elongated conduit 130 of catheter 100 is implanted into a patient's vascular system, while the hub 120 and connecting portions 110, 111 remain outside of the patient's body. The hub 120 optionally includes one or more suture holes 123, 124 for suturing the catheter 100 to the patient's skin. The proximal ends of the connecting portions 110, 111 include connecting means, such as Luer fittings, to facilitate connection to a fluid source to be delivered into the patient, a pump, a suction source for aspirating fluids from the patient, or the like.

Figure 5:
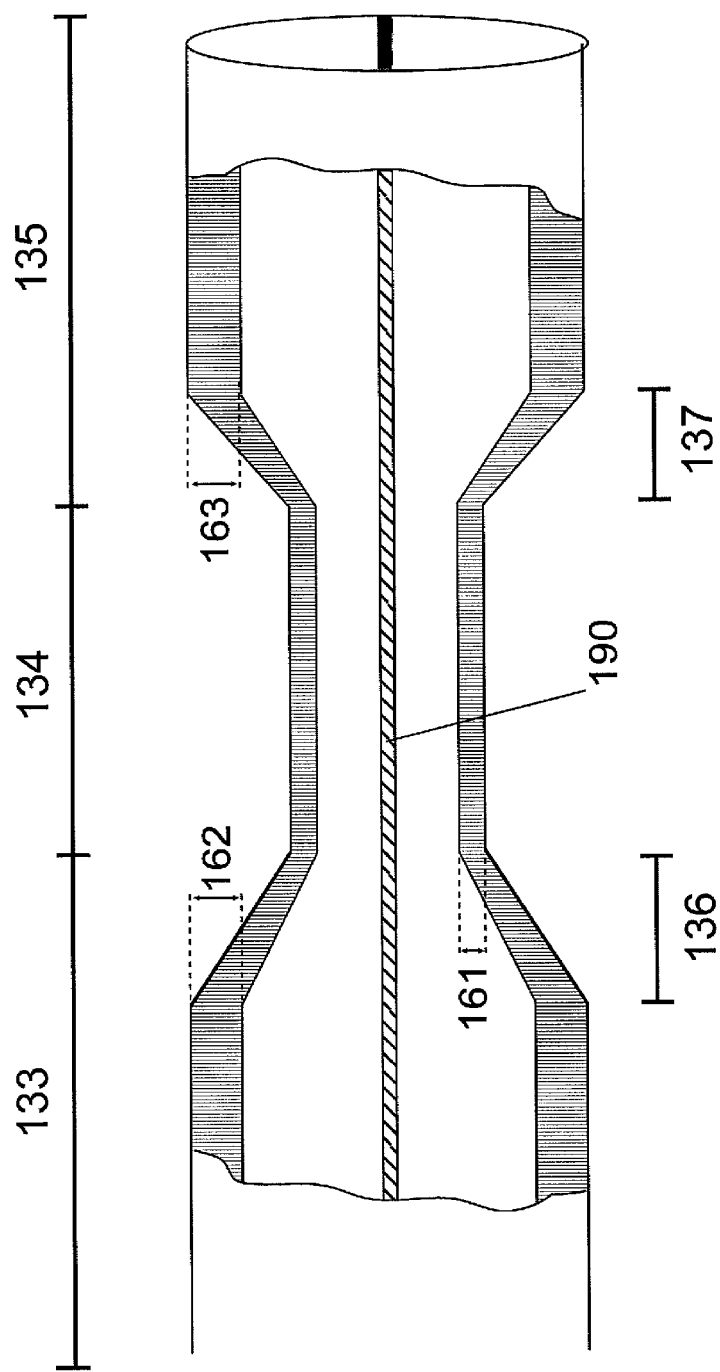
FIG. 5 is a cross-sectional view of a catheter device in accordance with an embodiment of the present invention.

As shown in FIG. 3d, the wall thickness 160 of the elongated conduit 130 is generally the distance between the outer wall and the inner lumen(s). In one embodiment, shown in FIG. 5, the wall thickness 161 of the intermediate conduit section 134 is less than the wall thicknesses 162, 163 of either or both of the proximal and distal conduit sections 133, 135. A greater wall thickness in the proximal and distal conduit sections 133, 135 can increase the strength and durability of the catheter where internal and external stresses are greatest. Where different wall thicknesses are used as described above, the wall thickness within the corresponding taper sections 136, 137 preferably gradually changes therebetween. In an alternate embodiment, the wall thickness 160 is substantially constant along the entirety of the elongated conduit 130.

Although the present invention is described herein with particular reference to PICCs, it should be recognized that aspects of the invention are equally applicable to other implantable catheter devices, such as dialysis catheters, midline catheters, central venous catheters, and ports.

The elongated conduit of the present invention is made from any suitable material, such as, for example, Polyether urethanes or Polyester urethanes, and preferably Polycarbonate urethanes such as those marketed under the Carbothane® mark by Lubrizol Corporation or the Quadrathane® mark by Biomerics, LLC. In an alternate embodiment, the elongated conduit of the present invention is made from a material that expands from a reduced delivery configuration into an expanded working configuration. For example, the elongated conduit, or just the proximal and/or distal conduit sections and corresponding taper section(s) thereof, may be made from a shape memory or other resilient or expandable polymeric material that is compressed to a small outer cross-sectional delivery dimension, and thereafter expands to an enlarged outer cross-sectional dimension to yield the configuration shown in FIG. 1. Such shape memory expansion may be triggered with heat (either by body temperature, or by heating with heating means such as a resistance wire); upon absorption of bodily or external fluids; by a chemical reaction with blood or other materials; by mechanical means such as the removal of a guidewire, delivery sheath, or other compression device; or by the application of an electrical current. As a non-limiting example, the use of expandable materials could allow for the delivery of a 5 French (F) catheter into a patient's vasculature such that it traverses through the venous system to the superior vena cava. Upon placement to the desired location, the proximal and distal conduit sections could expand to 7 F while the intermediate conduit section remains at 5 F, thus yielding the catheter configuration illustrated in FIG. 1 with the distal conduit section placed within the superior vena cava and the intermediate conduit section remaining in smaller blood vessels.

Figure 4:
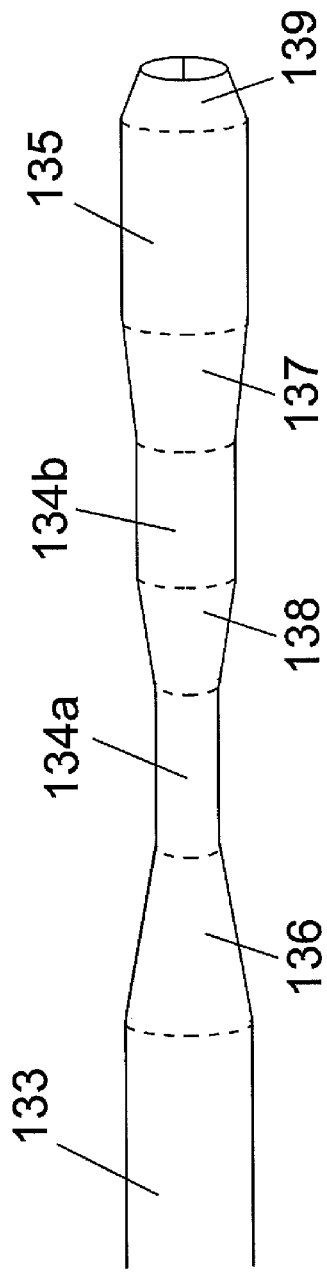
FIG. 4 is a side view of a catheter device embodiment of the present invention.

The embodiment illustrated in FIGS. 1-3 includes up to three sections with different outer cross-sectional dimensions and lumen cross-sectional dimensions, as previously described. In other embodiments, the catheters of the present invention comprise elongated conduits that include more than three such sections. For example, in the embodiment illustrated in FIG. 4, the elongated conduit 130 includes a proximal conduit section 133, a distal conduit section 135, and multiple intermediate conduit sections 134a and 134b. Preferably, an additional taper section 138 connects the intermediate conduit sections 134a and 134b. The elongate conduit 130 also optionally includes a distal taper 139 extending to the distal end 132, to provide an atraumatic tip.

Figure 6:
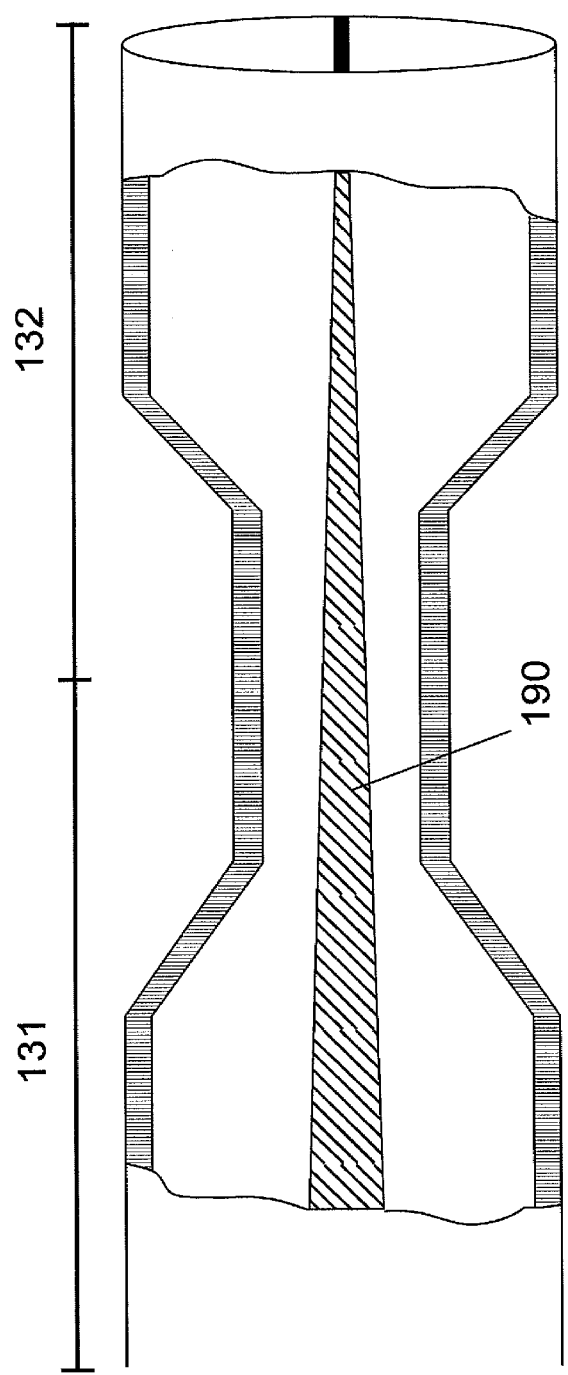
FIG. 6 is a cross-sectional view of a catheter device in accordance with an embodiment of the present invention.

In the embodiment of FIGS. 1-3, for the entire length of the elongated conduit 130, the internal divider 190 is of a constant thickness. In an alternate embodiment of the invention shown in FIG. 6, the internal divider 190 of the elongated conduit 130 thins in a distal direction along its length. Thickness of the internal divider is tapered so that it is thicker in a section of conduit closer to the proximal end 131 than it is in a section of conduit closer to the distal end 132. This change in thickness may be accomplished without reducing the cross-section of the lumen and thus restricting flow. The added thickness enables the internal divider in the proximal section to remain fixed in position when exposed to high differential pressures exerted in this region during dialysis or other procedures. Of course other embodiments of the invention, such as catheters with conduits conical along their length from a hub to an opening or to the conduit end, may also have this change in internal divider thickness from proximal end to distal end.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

We claim:

1. A flexible catheter for fluid access to a vascular system, the catheter comprising:
 a hub; and
 an elongated conduit comprising a flexible polymer, a proximal end, a distal end, and at least one lumen therein extending from the proximal end to the distal end, the proximal end coupled to the huh and the distal end having an opening in communication with the at least one lumen, the at least one lumen comprising:
  a proximal lumen section at the proximal end of the conduit, a distal lumen section at the distal end of the conduit, and an intermediate lumen section extending between said proximal and distal lumen sections;
 wherein a cross-sectional dimension of the intermediate lumen section is less than a cross-sectional dimension of the distal lumen section, and the cross-sectional dimension of the intermediate lumen section is less than a cross-sectional dimension of the proximal lumen section, and the cross-sectional dimension of the intermediate section is less than a cross-sectional dimension of the distal end opening; and
 wherein the elongated conduit comprises a first wall and a second wall, the first wall having a proximal section, an intermediate section, and a distal section, the intermediate section of the first wall having a wall thickness that is less than a proximal section of the first wall, and the intermediate section of the first wall having a wall thickness that is less than the distal section of the first wall, the second wall having a uniform wall thickness along the entire length of the elongated conduit.

2. The catheter of claim 1, wherein the cross-sectional dimension of the distal lumen section tapers to the cross-sectional dimension of the intermediate lumen section.

3. The catheter of claim 1, Wherein the cross-sectional dimension of the proximal lumen section tapers to the cross-sectional dimension of the intermediate lumen section.

4. The catheter of claim 3, wherein a proximal conduit section comprises the proximal lumen section, a distal conduit section comprises the distal lumen section, and an intermediate conduit section comprises the intermediate lumen section.

5. The catheter of claim 4, wherein each of the proximal, intermediate, and distal conduit sections comprise an outer cross-sectional dimension.

6. The catheter of claim 5, wherein the outer cross-sectional dimension of the intermediate conduit section is less than the outer cross-sectional dimension of either of the proximal or distal conduit sections.

7. The catheter of claim 6, wherein each of the outer cross-sectional dimensions of the proximal and distal conduit sections taper to the outer cross-sectional dimension of the intermediate conduit section.

* * * * *